(12) United States Patent  
Hem

(10) Patent No.: US 7,758,497 B2
(45) Date of Patent: Jul. 20, 2010

(54) ENDOSCOPIC ATTACHMENT DEVICE

(75) Inventor: Søren Hem, Minsk (BY)

(73) Assignee: Contura A/S, Soborg (DK)

( * ) Notice: Subject to any disclaimer, the term of this patent is extended or adjusted under 35 U.S.C. 154(b) by 592 days.

(21) Appl. No.: 10/872,231

(22) Filed: Jun. 18, 2004

(65) Prior Publication Data

US 2005/0049459 A1 Mar. 3, 2005

Related U.S. Application Data

(60) Provisional application No. 60/479,725, filed on Jun. 20, 2003.

(51) Int. Cl.
*A61B 1/00* (2006.01)
(52) U.S. Cl. ............ 600/121; 600/104; 600/105; 600/122; 600/123; 600/124; 600/137; 600/153; 600/154; 600/156; 600/158
(58) Field of Classification Search ......... 600/153–159, 600/104, 137
See application file for complete search history.

(56) References Cited

U.S. PATENT DOCUMENTS

| | | | | |
|---|---|---|---|---|
| 2,129,391 | A | * | 9/1938 | Wappler ............... 600/104 |
| 4,877,033 | A | | 10/1989 | Seitz, Jr. |
| 4,920,961 | A | * | 5/1990 | Grossi et al. ............. 606/14 |
| 4,998,527 | A | | 3/1991 | Meyer |
| 5,020,514 | A | | 6/1991 | Heckele |
| 5,287,845 | A | | 2/1994 | Faul et al. |
| 5,313,934 | A | | 5/1994 | Wiita et al. |
| 5,320,091 | A | | 6/1994 | Grossi et al. |
| 5,486,155 | A | * | 1/1996 | Muller et al. ............ 600/137 |
| 5,509,892 | A | * | 4/1996 | Bonnet ................... 600/156 |
| 5,575,756 | A | * | 11/1996 | Karasawa et al. ........ 600/157 |
| 5,947,994 | A | * | 9/1999 | Louw et al. ............. 606/200 |
| 6,053,860 | A | | 4/2000 | Brooks |
| 6,282,442 | B1 | * | 8/2001 | DeStefano et al. ......... 604/21 |
| 6,358,200 | B1 | * | 3/2002 | Grossi .................... 600/156 |
| 6,682,477 | B2 | * | 1/2004 | Boebel et al. ............ 600/107 |

FOREIGN PATENT DOCUMENTS

| | | |
|---|---|---|
| DE | 42 37 850 A1 | 5/1994 |
| GB | 2 284 158 A | 5/1995 |
| WO | WO 94/28782 | 12/1994 |
| WO | WO 99/47096 | 9/1999 |

OTHER PUBLICATIONS

EP, Standard Search Report dated Mar. 10, 2004, 4 pages.

\* cited by examiner

*Primary Examiner*—Matthew J Kasztejna
(74) *Attorney, Agent, or Firm*—Hunton & Williams LLP

(57) ABSTRACT

A sheath device (1) suitable for endoscopic instruments (2) and comprising an elongated tubular member (4) having a proximal end (6), a distal open end (7), and at least one fluid channel (23). A flushing unit (5) is connected to the proximal end (6) of the tubular member (4) and comprises a proximal open end (8) suitable for receiving a first endoscopic instrument (2), a fluid inlet (16) in contact with said fluid channel (23), and a fluid outlet (17). The tubular member and the flushing unit together define a first interior guiding passage (10) for sheathing at least a part of said first endoscopic instrument (2). The connection between the tubular member (4) and the flushing unit (5) allows for axial rotation of the tubular member (4) in relation to the flushing unit (5).

59 Claims, 3 Drawing Sheets

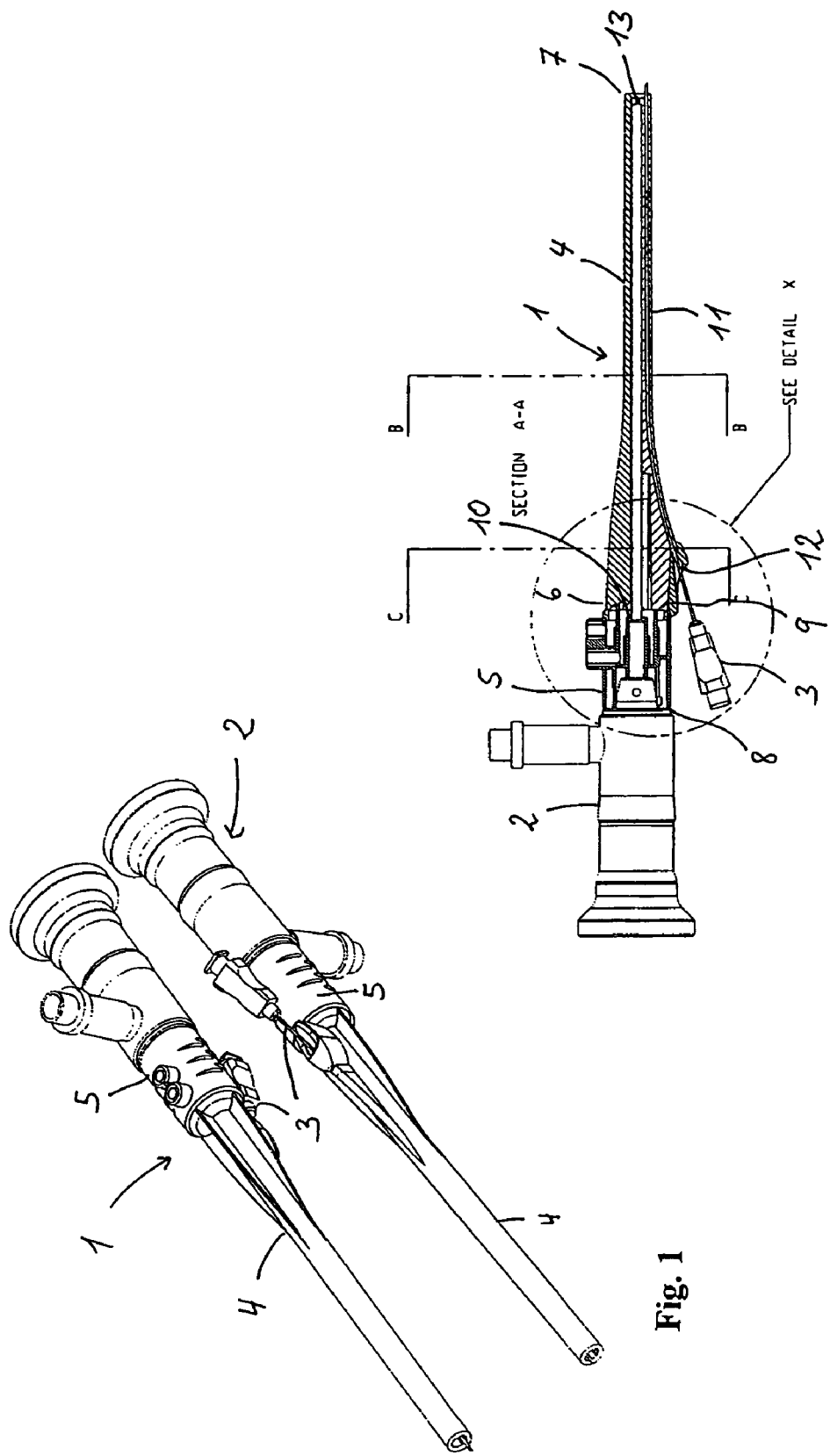

ENDOSCOPIC ATTACHMENT DEVICE

CROSS-REFERENCE TO RELATED APPLICATIONS

The present application claims priority to U.S. Provisional Patent Application No. 60/479,725 filed Jun. 20, 2003, which is hereby incorporated by reference in its entirety.

FIELD OF THE INVENTION

The present invention relates to a sheath device suitable for an endoscopic device, such as a catheter or cystoscope, which, said sheath when mounted onto any optical device, allows for the surgeon to examine or manipulate within an orifice or through a incision, whilst easily manipulating the endoscopic device. The device allows for delivery by means of an agent to the target organ or tissue at variable positions whilst maintaining a fixed position of the optical device or fluid inlet/outlet device.

BACKGROUND OF THE INVENTION

In medical practise, whether for purposes of examination or surgical procedures, the devices used in the practice must allow for the surgeon to easily interact with the patient's organs and cavities. Devices cumbersome to handle or manipulate may result in unsuccessful surgical procedures, misdiagnoses and, particularly in the case where the patient is not anaesthetised, great discomfort to the patient.

UK 2 284 158 discloses an injection catheter consisting of an outer sheath and a needle means located in and axially movable with relation to the outer sheath. Thus, when performing multiple injections, retraction of the needle means and rotation of the outer sheath is required. Moreover, the device does not allow for visualisation during the medical procedure.

WO 99/47069 discloses an instrument for guiding delivery of an injectable material for treating urinary incontinence. The device does not allow for variable positions of injection nor for visualisation during the medical procedure.

U.S. Pat. No. 5,020,514 discloses an endoscope for nasal surgery. Said endoscope comprises an outer shaft with a handle incorporating a switching valve for connecting/disconnecting a source of negative pressure and a source of a flushing fluid. A working insert, for insertion into the outer shaft, comprising a shaft for receiving an optical system, proximally connected to the working insert, a shaft for receiving an auxiliary instrument, and two guides for wires and rods, which are movable by means of handles.

U.S. Pat. No. 5,287,845 describes an endoscope for transurethral surgery, which has a main body irrotationally supporting an optic and a surgical instrument, an outer tube affixed to the main body and tubularly enclosing the optics and the surgical instrument. The outer tube is rotational relative to the remaining endoscope parts.

DE 42 37 850 discloses a device and method for injection/application of a fluid/medicament carrier, such as polyacrylamide, for medical use.

Further devices representative of the state of the prior art are described in WO 94/28782, U.S. Pat. No. 4,877,033, U.S. Pat. No. 5,313,934, and U.S. Pat. No. 5,320,091.

There is a need in the art for a device which, when attached to an optical device, allows for manipulation of the working element, namely the elements contacting with the patient, whilst allowing other elements, typically connected to fixed units in the operating theatre, to remain immobile. This allows for the surgeon to simply manipulate the working element whilst at once being visually aware of the interaction between the element inserted into the patient with the patient and being free from other cumbersome attachments.

SUMMARY OF THE INVENTION

A first aspect of the invention relates to a sheath device (1) suitable for endoscopic instruments (2), the device comprising:
  a) an elongated tubular member (4) comprising:
    a proximal end (6),
    a distal open end (7),
    at least one fluid channel (23) extending longitudinally from said proximal end to a fluid exit; and
  b) a flushing unit (5) connected to said proximal end (6) of the tubular member (4) and comprising:
    a proximal open end (8) suitable for receiving a first endoscopic instrument (2),
    a fluid inlet (16) being in contact with said fluid channel (23), and
    a fluid outlet (17),
  the tubular member and the flushing unit together define a first interior guiding passage (10) extending longitudinally from the proximal open end (8) of the flushing unit (5) to the distal open end (7) of the tubular member (4) for sheathing at least a part of said first endoscopic instrument (2), and wherein the connection between the tubular member (4) and the flushing unit (5) allows for axial rotation of the tubular member (4) in relation to the flushing unit (5).

A further aspect of the invention relates to the use of the device of the invention for the examination or surgical treatment of a mammalian body, such as a human. The invention similarly relates to a method of treating or examining an internal organ of a mammalian body comprising the use of the device A further aspect of the invention relates to a method of injecting a material into the human body comprising the use of the device of the invention. The invention further relates to a kit comprising the device and a material suitable for injection into the human body, such as a polymeric hydrogel comprising polyacrylamide.

A further aspect of the invention relates to a device for use in the examination or surgical treatment of a mammalian body, such as a human.

DESCRIPTION OF THE INVENTION

It is an object of the present invention to provide an endoscopic device that allows for the surgeon to manipulate the working element during operation and/or diagnosis while keep non-working elements immobile.

Further, it is an object of the present invention to provide for a sheath of an endoscopic equipment which needs minimal sterilisation and is disposable.

According to the invention, the above objectives is fulfilled by a sheath device suitable for endoscopic instruments, the device comprising:
  a) an elongated tubular member comprising:
    a proximal end,
    a distal open end, and
    at least one fluid channel extending longitudinally from said proximal end to a fluid exit; and
  b) a flushing unit connected to said proximal end of the tubular member and comprising:

a proximal open end suitable for receiving a first endoscopic instrument, a fluid inlet being in contact with said fluid channel, and a fluid outlet, the tubular member and the flushing unit together define a first interior guiding passage extending longitudinally from the proximal open end of the flushing unit to the distal open end of the tubular member for sheathing at least a part of said first endoscopic instrument, and wherein the connection between the tubular member and the flushing unit allows for axial rotation of the tubular member in relation to the flushing unit.

The term "internal organ" is intended to mean an organ, tissue or any cellular structure located inside the body cavity.

The term "endoscopic instrument" is intended to mean any kind of scope for surgery or diagnosing of internal cavities of a human body.

In a preferred embodiment, the elongated tubular member and the flushing unit each comprises an interior guiding passage, which together define said first interior passage, when the two elements are connected to each other. Thus, the first endoscopic instrument may be received through the proximal open end of the flushing unit and pushed into the guiding passage. The first endoscopic instrument may be a lens for viewing internal tissue or organs during operation or diagnosing, said instrument being coupled to a camera that may be connected to a television/screen.

The tubular member sheaths at least the part of the endoscopic instrument to be positioned inside the body, and while sheathing said part, the open distal end of the tubular member is introduced e.g. through a cavity in the body into the tissue or organ.

The sidewall of tubular member may have a smooth outer surface so as to expose the patient for as less pain as possible, when introducing it into the cavity, e.g. the urethra, vagina or rectum. Preferably, the cross-section perpendicular to the longitudinal direction of the tubular member is substantially circular, but it may be substantially oval shaped. The entire tubular member or just the part which is to be introduced to the body, e.g. 5-15 cm of the tubular member (measured from the distal end), may have a circular or an oval outer cross-section.

The diameter of the tubular member may differ depending on the sort of endoscopy, such as from 3 mm and up to 15 mm. For treatment of incontinence, the diameter of the part, which is to be introduced through the urethra, is preferably 7-8 mm.

Also the length of the tubular member may vary depending of the sort of endoscopy, so the length can be e.g. 5-30 cm, such as 10-25 cm, such as 15-20 cm.

The flushing unit is arranged for providing a flush of water (or other fluids) through the fluid exit, which preferably is located near said distal end or in said distal end. The flush may be used for flushing e.g. removed tissue or bone parts out of the body during an operation, or for flushing e.g. the bladder when operating for incontinence. The fluid channel is preferably placed between said interior guiding passage and the sidewall of the tubular member, but it may be placed separately inside the interior guiding passage of the tubular member. The diameter of the outlet may be larger than the diameter of the inlet.

In case the sheath device e.g. is used for treatment of anal incontinence, it is not needed to flush water into the rectum and therefore the flushing unit may be removed. Thus, the sheath device may in this case be rotationally connected directly to the endoscopic instrument.

The fluid exit is preferably positioned in the distal open end, but alternatively it may comprise one or more holes provided in the sidewall near the distal open end of the tubular member, so that the water exits the tubular member in an angle in relation to the longitudinal direction of the tubular member.

The tubular member and the flushing unit are preferably fixed (but still rotatable) connected to each other, but they may be detachable connected so that the two elements can be separated.

In a preferred embodiment of the invention, the tubular member further comprises a second guiding passage extending substantially longitudinal from a location near the proximal end or from the proximal end to the distal end of the tubular member, the second passage being suitable for receiving and guiding a second endoscopic instrument.

As the second guiding passage is positioned in the tubular member, it allows for rotation of the second endoscopic instrument in relation to the first endoscopic instrument and flushing unit. This is a major advantage during operation, as an endoscopic operation requires movement and rotation of one or more of the instruments positioned inside the body during the operation, and which can be complicated to control. As the second guiding passage can be rotated separately, the surgeon only needs to move the tubular member with the second instrument and not the flushing unit and first endoscopic instrument, when moving the second instrument e.g. from one tissue area to another. This provides an easier handling of the equipment and a less painful operation for the patient.

In particular, the second guiding passage is useful when treating a patient for incontinence. This treatment comprises i.a. the step of injecting a bulking agent in different tissue areas of the urethra near the bladder neck. In that case, the first instrument may comprise a lens and second instrument may comprise a needle to be introduced to the tissue, the needle being guided into the second guiding passage upon introducing the tubular member into the bladder through the urethra. The needle is introduced to the tissue area and the bulking agent injected, and if the surgeon wants to inject agent in another tissue area, he/she, may just retract the needle from the tissue, rotating the tubular member without moving the lens and flushing unit, and introducing the needle in another tissue area. Thus, the surgeon can maintain the lens in the same orientation while moving the needle (by the tubular member) inside the body.

The tubular member may be rotatable within an angle range of 0° to 360° in relation to said flushing unit, such as 45° or 90°. The connection between the tubular member and the flushing unit may comprise indicating means for indicating the axially angular rotation between the tubular member and the flushing unit+the first instrument.

Preferably, the second guiding passage comprises an inlet in its end closest to said proximal end of the tubular member, the inlet being arranged in an outer surface of said tubular member. The inlet may be substantially conical shaped so as to provide a better guidance of said second instrument into the passage. The inlet may comprise a penetrable sealing to be penetrated by the instrument. Preferably, inlet may comprise the conical shaped inlet made of rubber.

In order to improve the bending moment of the tubular member and thus prevent a breakage of the member, it may comprise reinforcement ribs extending on the outer surface of the tubular member from its proximal end and along at least a part of the tubular member towards the distal end. The inlet of the second guiding passage may be incorporated in one of the reinforcement ribs.

The second endoscopic instrument may comprise a needle, such as a needle for injecting bulking agent or another medical, the needle being flexible over a substantial portion of its length. The needle may be an ablation needle having cutting edge(s) for ablating and/or penetrating tissue.

Alternatively, the second instrument may comprise a fibre optic probe for operation of internal tissue.

Preferably, the sheath device may be disposable (onetime use) in order to provide a surgical equipment that requires as less sterilisation time as possible. Also the flushing unit may be disposable, in particular if the tubular member and the unit is fixed connected to each other.

In order to prevent reuse of the disposable sheath device and the flushing unit, a rubber sealing may be provided e.g. between the flushing unit and the tubular member, the rubber sealing being destroyed when exposing the sheath device to a sterilisation process e.g. in an autoclave.

The flushing unit is provided for the purpose of flushing water into the internal organ of the body so as to flush out removed tissue or bone parts. The fluid inlet may be connected to a water reservoir via a flexible tube for flushing clean water through the fluid channel and out of said fluid exit into the organ. The outlet may also be connected via a flexible tube to another water reservoir for flushing filthy water away from the internal organ via said interior passage.

The fluid outlet may be in contact with said open distal end of the tubular member via an interior passage extending longitudinally in said tubular member. Preferably, the interior passage is composed by the first guiding interior guiding passage of the tubular member, the diameter of which being larger than the diameter of the endoscopic instrument introduced therein. Thus, filthy water may flow into said distal open end, along the outer surface of the endoscopic instrument and out through the outlet. Alternatively, the outlet may be in contact with the distal open end via a separate passage/fluid channel provided in the tubular member.

In a preferred embodiment, the flushing unit comprises an inner tube and an outer tube surrounding the inner tube with a space therebetween. The inlet is connected to the space created between the outer and inner tube, and the outlet is connected to the space inside the inner tube. When assembling the flushing unit with tubular member, the inner tube will be connected to the first guiding passage, and the outer tube will be connected to the fluid channel(s). Thus, when e.g. flushing the bladder and/or urethra the fluid that exits the distal end of the tubular member will be flushed back into the first interior guiding passage without applying a suction in the first passage. This is a substantially faster process than for devices described in the prior art where flushing and suction are turned on separately.

However, a suction may be provided in the first guiding passage so that the fluid is sucked out of the bladder and/or urethra.

The first interior guiding passage of the flushing unit may be arranged coextendingly inside the inner tube, so that this passage is connected to the interior guiding passage of the tubular member when connecting the flushing unit thereto. Thus, the first interior guiding passage, extending longitudinally from the proximal open end of the flushing unit to the distal open end of the tubular member for sheathing at least a part of said first endoscopic instrument, is defined, cf. claim 1.

The proximal open end of the flushing unit is suitable for receiving and guiding the first endoscopic instrument into said interior guiding passage. Sealing means may be provided in said proximal open end of the flushing unit to obtain a tight connection to the endoscopic instrument.

The first and second guiding passages and the fluid channel preferably extends substantially parallel to each other. When seeing the tubular member in the cross-section perpendicular to its longitudinal direction, it may have a honeycomb-like cross-section, wherein the first guiding passage is provided in the middle (on the centre line of the tubular member) and the fluid channel(s), second guiding passage or more guiding passages are provided between the first guiding passage and the sidewall of the tubular member.

Due to ease of production of the sheath device, the fluid channel and guiding passages may provided by a detachable wall member positioned inside the tubular member, and which is not moulded simultaneously with the tubular member, but inserted therein afterwards. The detachable wall member may, together with the sidewall of the tubular member, define said fluid channel(s) and passages.

The tubular member may comprise two or three further longitudinal extending guiding passages for further endoscopic instruments.

The distal end of the tubular member may comprise a circumferential inwardly extending bulge for guidance of a distal end of said second endoscopic instrument, in particular the abovementioned flexible needle. The bulge is useful in connection with the abovementioned treatment for incontinence, because the distal end of the needle can be bend, so as to provide an even better control of the needle tip. The bulge may bend the distal end of the needle such that it may emergence the tubular member at angle of 5-45° in relation to the centre line of the tubular member.

Depending on the sort of endoscopic operation/diagnosing, the sheath device may be suitable for different kinds of endoscopic instrument. The instruments to be introduced to the first interior guiding passage may comprise a cystoscope or a gastroscope or an ureteroscope or a resectoscope or an arthroscope or a telescope or an obturator.

The first endoscopic instrument may also comprise a camera lens e.g. for viewing internal tissue or organs. The lens is connected to a camera so that the surgeon can view the inside of the body on a screen. Due to the second guiding passage, the surgeon only has to look at the screen and not on the endoscopic equipment, as the passage guides e.g. the needle.

The lens may be disposable (onetime use). A type of lens used for this purpose could be the sort of lenses used in the "night vision goggles" in the military. The disposable lens may be incorporated in the tubular member, so that the surgeon only has to connect the sheath device to the endoscopic instruments needed for the operation and connect the lens to a camera. After the operation, the sheath device with the lens incorporated is thrown away, and the sterilisation process is dispensed with.

Preferably, the distal end of the tubular member exceeds a distal end of the lens, so that the surgeon, when introducing an instrument through the second guiding passage, may view the tip of the instrument on the screen, before the instrument is introduced into the tissue or organ.

When treating for incontinence known methods and equipment require a visual survey meaning that the surgeon need to view an outflow of urine before knowing the right location to be treated in the bladder neck. As the sheath device according to the invention allows for use of both a camera lens and an injection needle at the same time, a visual survey is dispensed with, as the surgeon can find the right location to be treated on the television/screen.

The sheath device may be made of an appropriate plastic material or a metal.

A generally interesting aspect of the invention relates to a method of injecting a material into the human body comprising the use of the device of the invention.

A very interesting aspect of the invention relates to a kit comprising i) the device of the invention; ii) a material suitable for injection into the human body. The material is selected from the group consisting of silicone, hyaluronic acid, polyacrylamide hydrogel, soya, alginates such as modified alginates, bacterial polysaccharides such as gellan gum, plant polysaccharides such as carrageenans, hyaluronic acids, polyethylene oxide-polypropylene glycol block copolymers, proteins such as fibrin, collagen, and gelatin, mixtures of polyethylene oxide and polyacrylic acid, cross-linked chitosan, photochemically cross-linked ethylenically unsaturated groups, macromers such as PEG-oligolactyl-acrylates, polyethylenimine, poly-lysine, poly(vinylamine), and poly(allylamine). In a preferred embodiment, the material is polyacrylamide and derivatives thereof.

Suitable material, may be selected from Metacril, Dermagen, Evolution®, OutLine®, Formacryl®, Argiform®, Bioformacryl, DermaLive, DermaDeep®, Amazing Gel, Bioplastique®, Artecoll®, Arteplast®, Silicone Injections, Profill or Profil, Aquamid®, BioAlcamid™, Radiance (by Bioform) or derivatives thereof or materials of essentially the same chemical composition.

As stated, in a preferred embodiment, the material is polyacrylamide and derivatives thereof, most preferably wherein the cross-linked polyacrylamide was prepared from methylene-bis-acrylamide.

A further aspect of the invention relates to a device for use in the examination or surgical treatment of a mammalian body, such as a human.

A further aspect of the invention relates to the use of a device of the present invention for the examination or surgical or diagnostic treatment of a mammalian body, such as a human. The invention relates to a method of treating or examining an internal organ of a mammalian body comprising the use of the device of the invention.

In a typical embodiment, the method of the invention relates to a method of treating, examining or diagnosing a urogenitial organ comprising the use of the device of the present invention. In a typical aspect of the invention, the invention relates to a method of performing a gynealogical examination, typically on a woman, comprising the use of the device of the invention.

In a particularly interesting aspect, the invention is directed to a method of treating incontinence comprising the use of the device of the invention, typically urinary incontinence or anal incontinence.

In a further aspect, the invention is directed to a method of treating an articular joint in a mammal comprising the use of the device of the invention.

In a further aspect, the invention is directed to a method of treating vesicouretal reflux comprising the use of the device of the invention.

In a further aspect, the invention is directed to a method of treating reflux esophagitis comprising the use of the device of the invention.

In a further aspect, the invention is directed to a method of treating arthritis comprising the use of the invention. Similarly, in a further aspect, the invention is directed to a method of treating tendonitis comprising the use of the device of the invention.

In a preferred embodiment, the hydrogel of the invention is for use in the treatment of urinary and anal incontinence, more preferably urinary incontinence.

Urinary incontinence may be stress or reflex urinary incontinence or urge urinary incontinence. Typically, the hydrogel of the invention is suitable for the treatment of stress or reflex urinary incontinence.

In a further aspect of the invention, the present hydrogel is used in the preparation of an endoprosthesis. Thus, a further object of the invention is the use of a hydrogel, as described supra, comprising about 0.5 to 25% by weight polyacrylamide, based on the total weight of the hydrogel, for the preparation of an endoprosthesis for the treatment and prevention of incontinence and vesicouretal reflux.

The endoprosthesis is suitably formulated as an injectable suspension. The suspension comprises a homogenised formulation of the hydrogel. Typically, a syringe is filled with the suspension.

A further object of the invention relates to a method of treating or preventing incontinence or vesicouretal reflux comprising administering a hydrogel to a mammal said hydrogel comprising 0.5 to 25% by weight polyacrylamide, based on the total weight of the hydrogel. The hydrogel, in any of the above-described embodiments, is suitable for the method of the invention.

Upon administration of the hydrogel, a thin layer of connective tissue surrounds the endoprosthesis, enabling the endoprosthesis to become a stable part of the connective tissue. Due to the stability of the hydrogel and the thin layer of connective tissue, the endoprosthesis may be removed from the patient. This advantage is at least in part due to the stability of the hydrogel which in turn is at least in part due to the washing process.

Several factors affect the rheological properties of the hydrogel, such as the relative amount of monomer used, the relative amount of initiator, the temperature and other parameters of the polymerisation process, and the washing process. Thus, the polymerisation process may provide a hydrogel with an array of viscosities. The invention is directed to an endoprosthesis typically for the urethra, the rectum or colon (or canalis analis), or the ureter and may thus be tailored to the requirements of the conduit.

An important object of the invention is to provide a prosthetic device for increasing the resistance of conduits selected from the group consisting of the urethra; the rectum or colon (or canalis analis); and the ureter for the treatment of urinary incontinence, anal incontinence, and vesicouretal reflux, respectively; wherein said device is injectable and comprising the hydrogel as described herein.

The method of the invention preferably includes the administering of the hydrogel by means of injecting the hydrogel into the appropriate conduit. In the treatment of urinary incontinence, the hydrogel is typically injected into the urethra, specifically under the submucosal membrane of the urethra. Injection is via the external surface of the urethra and toward the submucosal membrane.

The present investigators have found that typically 2 to 5 mL of the hydrogel are suitable to provide adequate resistance in the urethra by bulking the urethra. Typically, 3 mL of hydrogel is injected and preferably the 2-5 mL are distributed by depositing the gel at more than one cross-sectional position along a single longitudinal position of the urethra. In a particularly suitable embodiment, 3 or more depots are made along a single longitudinal position of the urethra. The present investigators have found that depots 0.5 cm distally from the neck of the bladder are particularly suitable.

The present investigators have found that submucosal injections at positions 10, 2, and 6 o'clock of the cross-sectional axis of the urethra to be particularly suitable for the treatment of urinary incontinence.

The depots are typically made by means of a syringe or by use of a cytoscope or catheter. Suitably a 21 to 27 G needle is employed for the injection.

For the treatment of anal incontinence, the hydrogel is typically injected into the colon or rectum (canalis analis) specifically under the submucosal membrane of the colon or rectum. Injections of 2 to 6 ml are suitable. The hydrogel is preferably distributed at more than one cross-sectional position along a single longitudinal position of the colon or rectum. In a particularly suitable embodiment, 3 or more depots are made along a single longitudinal position of the colon or rectum, preferably at positions 10, 2, and 6 o'clock of the cross-sectional axis of the colon or rectum.

For the treatment of vesicouretal reflux, submucosal injections into the ureter of the patient is required. Injections of 2 to 5 ml are suitable. The hydrogel is preferably distributed at more than one cross-sectional position along a single longitudinal position of the ureter In a particularly suitable embodiment, 3 or more depots are made along a single longitudinal position of the ureter, preferably at positions 10, 2, and 6 o'clock of the cross-sectional axis of the ureter.

In an alternative embodiment of the invention, the method comprises the use of a prosthetic device comprising cells, such as stem cells. Polyacrylamide provides an excellent template and matrix for cell growth. The use of cells in combination with the hydrogel of the invention for the preparation of the device would allow for cellular engraftment to the surrounding tissue in the ureter, urethra or analis canalis. A method comprising the hydrogel of the invention and the appropriate cells allows for greater resistance and greater efficiency in providing resistance.

In a further embodiment of the invention, the device prosthetic device comprises cells, such as stem cells or fat cells. Polyacrylamide provides an excellent template and matrix for cell growth. The use of cells with the hydrogel of the invention for the preparation of the device would allow for cellular engraftment to the surrounding tissue in the ureter, urethra or analis canalis. A device comprising the hydrogel of the invention and the appropriate cells allows for greater resistance and greater efficiency in providing resistance.

DESCRIPTION OF THE FIGURES

A preferred embodiment of the invention will now be described with reference to the accompanying figures, wherein FIG. 1 shows the sheath device connected to a scope, FIG. 2 shows a cross-sectional view of the sheath device connected to a scope.

FIG. 1 shows a sheath device 1 connected to a scope 2, and an injection needle 3 is also introduced. The sheath device comprises a tubular member 4 and a flushing unit 5, which are detachably connected to each other in a way that allows rotation of the tubular member in relation to the flushing unit and scope.

FIG. 2 shows a cross-sectional view of the sheath device 1 connected to a scope 2. The tubular member has a proximal end 6 and a distal open end 7, the flushing unit 5 being connected to the proximal end 6. The flushing unit comprises a proximal open end 8 and a distal end 9 (see e.g. FIGS. 7-8), the proximal end 8 being adapted to receive said scope.

Figure 4:
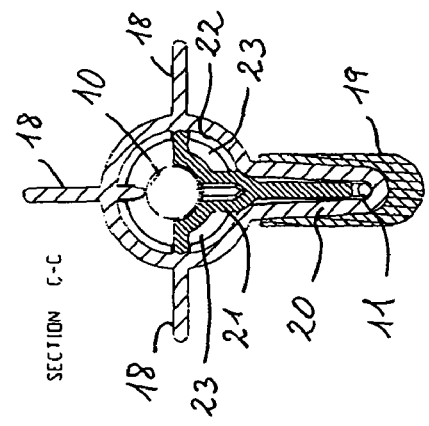
FIGS. 4-6 shows a cross-sectional view of the sheath device.

The tubular member 4 and the flushing unit 5 together define a first interior guiding passage 10 extending longitudinally from the proximal open end 8 of the flushing unit to the distal open end 7 of the tubular member for sheathing a part of the endoscopic instrument 2.

The tubular member further comprises a second guiding passage 11 extending substantially longitudinal from a location 12 near the proximal end or from the proximal end 6 to the distal end 7 of the tubular member, the second passage being suitable for receiving and guiding a second endoscopic instrument 3 (needle).

Figure 3:
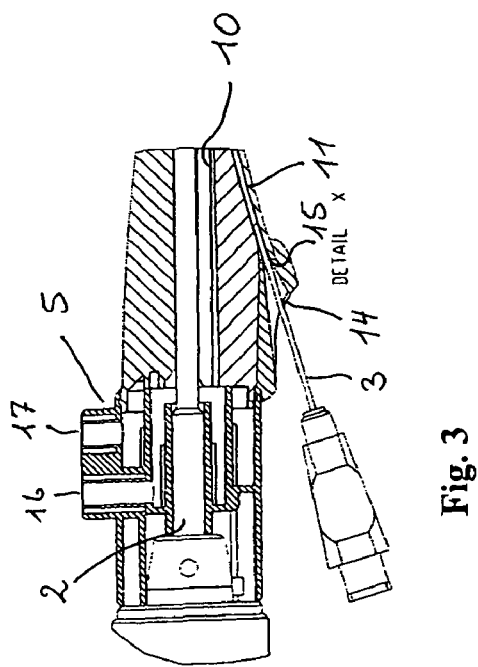
FIG. 3 shows cross-sectional view of the proximal end of the sheath device.

FIG. 3 shows detail X of FIG. 2, wherein the needle 3 is positioned in the second guiding passage 11, and the endoscope is positioned in the first guiding passage. The second guiding passage 11 comprises an inlet 14 in its end closest to said proximal end 6 of the tubular member 4, the inlet being arranged in an outer surface of said tubular member.

The inlet 14 is substantially conical shaped so as to guide said treatment instrument 3 into the passage. The inlet comprises a penetrable sealing 15 to be penetrated by the instrument 3. Preferably, inlet may comprise the conical shaped inlet made of rubber.

The flushing unit 5 comprises a fluid inlet 16 and a fluid outlet 17, the fluid inlet being in contact with the first guiding passage 10 which also may be used as fluid channel, and which comprises a fluid exit 13 in the distal open end of the tubular member, cf. FIG. 2.

FIG. 4 shows cross-section C-C of FIG. 2, which is a cross-section of the tubular member 4. The tubular member comprises reinforcement ribs 18 extending on its outer surface. The first guiding passage 10 is positioned such that its centre line is coincident with a centre line of the tubular member. The inlet 14 of second guiding passage 11 is positioned in a detachable rubber element 19 being slided over the rib 20.

A detachable wall member 21 is positioned inside the tubular member 4, and which is not moulded simultaneously with the tubular member, but inserted therein afterwards. The detachable wall member 21, together with the sidewall 22 of the tubular member, defines channels/passages 23.

Figure 5:
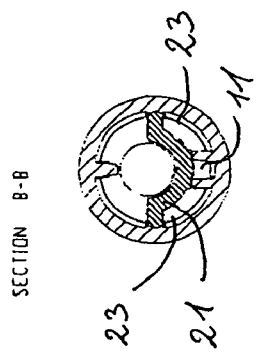

FIG. 5 shows cross-section B-B of FIG. 2, wherein the detachable wall member 21 defines channels 23 for fluid and/or instruments. The second guiding passage 11 is shown.

Figure 6:
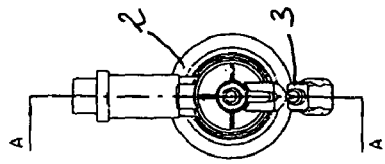

FIG. 6 shows cross-section A of FIG. 2, comprising the scope 2, the needle 3 and the tubular member 4.

Figure 7:
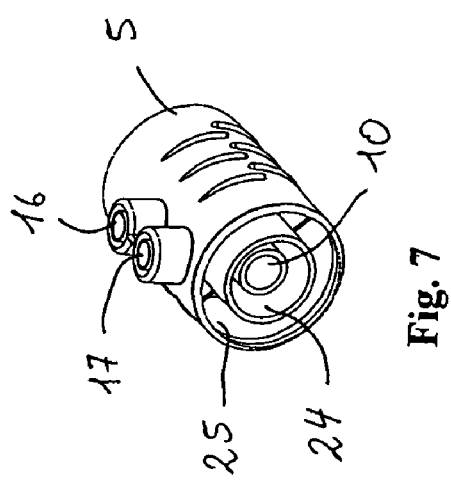
FIG. 7 shows a flushing unit according to the invention.

FIG. 7 shows the flushing unit 5 with the fluid inlet 16 and the fluid outlet 17, the inlet being in contact with the fluid channel 24 and the outlet being in contact with the fluid channel 25.

Figure 8:
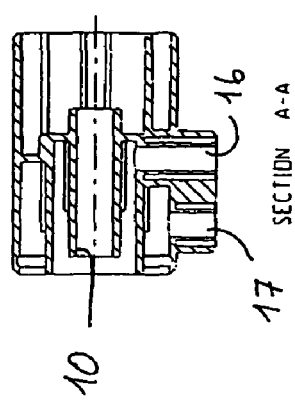

FIG. 8 shows a cross-section of the flushing unit comprising the inlet 16, the outlet 17 and the guiding passage 10.

Figure 9:
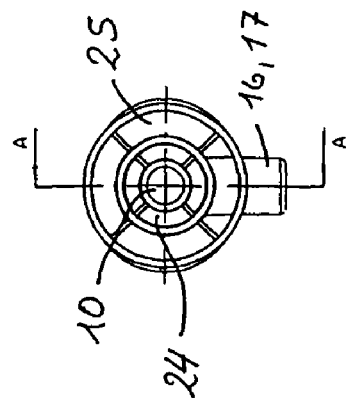
FIGS. 8-9 show cross-sectional view of the flushing unit.

FIG. 9 is a cross-section of the flushing unit taken perpendicular in relation to the cross-section of FIG. 8.

Figure 10:
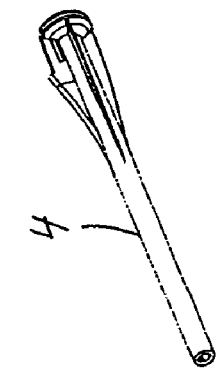
FIG. 10 shows an elongated tubular member according to the invention.

FIG. 10 shows the tubular member 4 of the sheath device.

Figure 11:
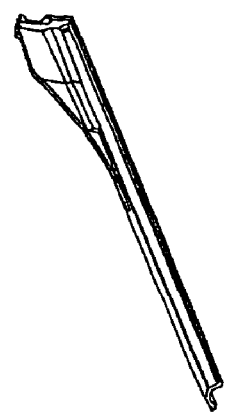
FIG. 11 shows a detachable wall member for providing a fluid channel and guiding passages.

FIG. 11 shows the detachable wall member 21 for providing fluid channels and/or guiding passages within the tubular member 4, see description of FIG. 4 above.

The present invention is not to be limited in scope by the specific embodiments described herein. Indeed, various modifications of the present invention, in addition to those described herein, will be apparent to those of ordinary skill in the art from the foregoing description and accompanying drawings. Thus, such modifications are intended to fall within the scope of the following appended claims. Further, although the present invention has been described herein in the context of a particular implementation in a particular environment for a particular purpose, those of ordinary skill in the art will recognize that its usefulness is not limited thereto and that the present invention can be beneficially implemented in any number of environments for any number of purposes.

The invention claimed is:

1. A sheath device suitable for medical usage in endoscopic instruments, the device comprising:
   a) an elongated tubular member comprising:
   a proximal end,
   a distal open end, and
   a sidewall extending between the proximal end and the distal open end, and
   at least one fluid channel extending longitudinally from said proximal end to a fluid exit; and
   b) a flushing unit connected to said proximal end of the tubular member and comprising:
   a proximal open end suitable for receiving a first endoscopic instrument,
   a fluid inlet being in contact with said fluid channel, and
   a fluid outlet,
   wherein the tubular member and the flushing unit together define a first interior guiding passage extending longitudinally from the proximal open end of the flushing unit to the distal open end of the tubular member for sheathing at least a part of said first endoscopic instrument,
   wherein the tubular member further comprises a second guiding passage extending substantially longitudinally from a location near the proximal end or from the proximal end to the distal end of the tubular member, the second passage being suitable for receiving and guiding an injection needle,
   wherein the second guiding passage comprises an inlet in its end closest to said proximal end of the tubular member, the inlet being arranged in through an outer surface of the sidewall of the tubular member, such that an injection needle may be introduced through said second guiding passage,
   and wherein the connection between the tubular member and the flushing unit allows for axial rotation of the tubular member in relation to the flushing unit.

2. A device according to claim 1, wherein the inlet is substantially conical shaped so as to guide said injection needle into the passage.

3. A device according to claim 1, wherein the tubular member is disposable.

4. A device according to claim 1, wherein the flushing unit is disposable.

5. A device according to claim 1, wherein the tubular member and the flushing unit are fixedly connected to each other.

6. A device according to claim 1, wherein the tubular member and the flushing unit are detachably connected to each other.

7. A device according to claim 1, wherein the fluid exit is located near said distal end or in said distal end.

8. A device according to claims 1, wherein the fluid outlet is in contact with said open distal end of the tubular member via an interior passage extending longitudinally in said tubular member.

9. A device according to claim 8, wherein the interior passage is a part of said first interior guiding passage.

10. A device according to claim 1, wherein the guiding passages and the fluid channel extend substantially parallel to each other.

11. A device according to claim 1, wherein a center line of the first interior guiding passage is coincident with a centre line of the tubular member.

12. A device according to claim 1, wherein the first endoscopic instrument comprises a fiber optic probe.

13. A device according to claim 1, wherein said tubular member is freely rotatable within an angle range of 0° to 360° in relation to said flushing unit.

14. A device of claim 13, wherein said tubular member is rotatable within an angle range of 45° to 90°.

15. A device according to claim 1, wherein the fluid inlet is connected to a water reservoir for flushing clean water through the fluid channel and out of said fluid exit.

16. A device according to claim 1, wherein the fluid outlet is connected to a water tank for flushing wastewater away from the internal organ via said interior passage.

17. A device according to claim 1, wherein the tubular member comprises up to three further longitudinal extending guiding passages for further endoscopic instruments.

18. A device according to claim 1, wherein an outer diameter near said distal end of said tubular member is between 5-20 mm.

19. A device according to claim 1, wherein a cross-section perpendicular to the longitudinal direction of the tubular member is substantially oval shaped.

20. A device according to claim 1, wherein the length of the tubular member is 5-40 cm.

21. A device according to claim 1, wherein one or more of the fluid channel and guiding passages is provided by a detachable wall member positioned inside the tubular member.

22. A device according to claim 1, wherein the distal end of the tubular member comprises a circumferential inwardly extending bulge for guidance of a distal end of said injection needle.

23. A device according to claim 22, wherein said bulge is arranged to bend the distal end of the injection needle such that it may emerge from the tubular member at an of 5° to 45° in relation to the center line of the tubular member.

24. A device according to claim 1, wherein the first endoscopic instrument comprises a cystoscope, a gastroscope, an ureteroscope, a resectoscope, an arthroscope, a telescope or an obturator.

25. A device according to claim 1, wherein the first endoscopic instrument comprises a camera lens.

26. A device according to claim 25, wherein said lens is disposable.

27. A device according to claim 25, wherein the distal end of the tubular member exceeds a distal end of the lens.

28. A device according to claim 1, wherein the flushing unit comprises at least one tap positioned near either one or both of the inlet and outlet of the flushing unit.

29. A method of using the device according to claim 1 for the examination of a mammalian body.

30. A method of using the device according to claim 1 for the surgical treatment of a mammalian body.

31. A method of treating an internal organ of a mammalian body comprising the use of the device according to claim 1.

32. A method of examining an internal organ of a mammalian body comprising the use of the device according to claim 1.

33. A method of treating a urogenitial organ comprising the use of the device according to claim 1.

34. A method of examining a urogenital organ comprising the use of the device according to claim 1.

35. A method of treating an articular joint in a mammal comprising the use of the device according to claim 1.

36. A method of treating urinary incontinence comprising the use of the device according to claim 1.

37. A method of treating anal incontinence comprising the use of the device according to claim 1.

38. A method of treating vesicouretal reflux comprising the use of the device according to claim 1.

39. A method of treating reflux esophagitis comprising the use of the device according to any of claim 1.

40. A method of treating arthritis comprising the use of the device according to claim 1.

41. A method of treating tendonitis comprising the use of the device according to claim 1.

42. A method of performing a gynecological examination comprising the use of the device according to claim 1.

43. A method of injecting a material into the human body comprising the use of the device according to claim 1.

44. A device of claim 1, wherein an outer diameter near said distal end of said tubular member is between 10-15 mm.

45. A device of claim 1, wherein an outer diameter near said distal end of said tubular member is between 7-8 mm.

46. A device of claim 1, wherein a cross-section perpendicular to the longitudinal direction of the tubular member is substantially circular.

47. A device of claim 1, wherein the length of the tubular member is 10 to 35 cm.

48. A device of claim 1, wherein the length of the tubular member is 15 to 30 cm.

49. A device according to claim 1, wherein said inlet forms an acute angle with respect to said first interior guiding passage.

50. A device according to claim 1, wherein said interior passage in contact with said fluid outlet is separate from said fluid channel.

51. A device according to claim 50, wherein the interior passage in contact with said fluid outlet is a part of said first interior guiding passage.

52. A device according to claim 50, wherein a diameter of the first interior guiding passage of the tubular member is larger than the diameter of an endoscopic instrument introduced therein.

53. A device according to claim 52, wherein the flushing unit comprises
an inner tube; and
an outer tube surrounding the inner tube with a space there between,
wherein the fluid inlet is connected to the space between the outer and inner tube, and the fluid outlet is connected to a space inside the inner tube,
and wherein the inner tube connects to the first guiding passage, and the outer tube connects to the fluid channel.

54. A device according to claim 53, wherein the first interior guiding passage of the flushing unit is arranged coextendingly inside the inner tube, and connects to the interior guiding passage of the tubular member.

55. A sheath device suitable for endoscopic instruments, the device comprising
a) an elongated tubular member comprising:
a proximal end,
a distal open end, and
a sidewall extending between the proximal end and the distal open end, and
at least one fluid channel extending longitudinally from said proximal end to a fluid exit; and
b) a flushing unit connected to said proximal end of the tubular member and comprising:
a proximal open end suitable for receiving a first endoscopic instrument,
a fluid inlet being in contact with said fluid channel, and
a fluid outlet,
wherein the tubular member and the flushing unit together define a first interior guiding passage extending longitudinally from the proximal open end of the flushing unit to the distal open end of the tubular member for sheathing at least a part of said first endoscopic instrument,
wherein the fluid outlet is in contact with said open distal end of the tubular member via an interior passage extending longitudinally in said tubular member, said interior passage in contact with said fluid outlet being separate from said fluid channel,
wherein the tubular member further comprises a second guiding passage extending substantial longitudinally from a location near the proximal end or from the proximal end to the distal end of the tubular member, the second guiding passage being suitable for receiving and guiding an injection needle,
wherein the second guiding passage comprises an inlet in its end closest to said proximal end of the tubular member, the inlet being arranged through an outer surface of the sidewall of said tubular member, such that an injection needle may be introduced through said second guiding passage,
and wherein the connection between the tubular member and the flushing unit allows for axial rotation of the tubular member in relation to the flushing unit.

56. A device according to claim 55, wherein the interior in contact with the fluid outlet is a part of said first interior guiding passage.

57. A device according to claim 56, wherein a diameter of the first interior guiding passage of the tubular member is larger than the diameter of an endoscopic instrument introduced therein.

58. A device according to claim 57, wherein the flushing unit comprises
an inner tube; and
an outer tube surrounding the inner tube with a space there between,
wherein the fluid inlet is connected to the space between the outer and inner tube, and the fluid outlet is connected to a space inside the inner tube,
and wherein the inner tube connects to the first guiding passage, and the outer tube connects to the fluid channel.

59. A device according to claim 58, wherein the first interior guiding passage of the flushing unit is arranged coextendingly inside the inner tube, and connects to the interior guiding passage of the tubular member.

* * * * *

UNITED STATES PATENT AND TRADEMARK OFFICE
CERTIFICATE OF CORRECTION

PATENT NO. : 7,758,497 B2  Page 1 of 1
APPLICATION NO. : 10/872231
DATED : July 20, 2010
INVENTOR(S) : Soren Hem It is certified that error appears in the above-identified patent and that said Letters Patent is hereby corrected as shown below:

Claim 1, Column 11, line 37, please delete "in".

Signed and Sealed this

Fifth Day of October, 2010

David J. Kappos
*Director of the United States Patent and Trademark Office*